United States Patent [19]

Hokama et al.

[11] Patent Number: 5,698,694

[45] Date of Patent: Dec. 16, 1997

[54] PROCESS FOR PREPARING SUBSTITUTED PYRIMIDINES

[75] Inventors: Takeo Hokama, Mountain View; Ian S. Cloudsdale, Boulder Creek, both of Calif.; Werner Langer, Rheinfelden; Hermann Schneider, Heitersheim, both of Germany

[73] Assignee: Sandoz Ltd., Basel, Switzerland

[21] Appl. No.: 738,370

[22] Filed: Oct. 25, 1996

[51] Int. Cl.$^6$ .................. C07D 239/26; C07D 239/30; C07D 239/42; C07D 239/34

[52] U.S. Cl. .................. 544/319; 544/335; 544/334; 544/333; 544/326; 544/327; 544/328; 544/329; 544/242

[58] Field of Search .................. 544/319, 335, 544/334, 333, 326, 327, 328, 329, 242

[56] References Cited

U.S. PATENT DOCUMENTS 5,506,192  4/1996  Anderson et al. .................. 544/319

Primary Examiner—John M. Ford
Attorney, Agent, or Firm—Bell Seltzer Intellectual Property Law Group Alston & Bird LLP

[57] ABSTRACT

A process for preparation of substituted phthalides, heterocyclic phthalides and derivatives thereof by reacting an aromatic carboxylic acid mono- or di-anion with a reactive derivative of a pyrimidine carboxylic acid.

11 Claims, No Drawings

PROCESS FOR PREPARING SUBSTITUTED PYRIMIDINES

The present invention concerns a process for preparation of substituted phthalides, heterocyclic phthalides and derivatives thereof.

In particular, the invention concerns preparing substituted phthalides, heterocyclic phthalides and derivatives thereof by reaction of an aromatic carboxylic acid or reactive derivative thereof by forming a mono- or di-anion and reacting this with a reactive derivative of a pyrimidine carboxylic acid.

The present invention therefore provides a process for preparing a compound of formula I

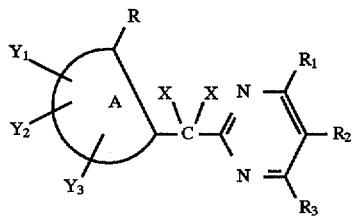

wherein,

A is phenyl or pyridyl,

R is a carboxyl group which may be in the form of the free acid or in ester or salt form, a thiocarboxyl group which may be in the form of the free acid or in ester form or a di-substituted carbamoyl group, $Y_1$, $Y_2$ and $Y_3$ are independently hydrogen or halogen;

$R_1$, $R_2$, and $R_3$ each is independently hydrogen; halogen; alkyl, alkenyl, alkynyl, alkoxy, alkenyloxy, alkynyloxy, alkylthio, alkenylthio or alkynylthio, each of which may in turn be substituted by 1 to 6 halogen atoms; cycloalkyl, heterocycloalkoxy, aryloxy, aralkoxy or aralkylthio each of which may be substituted by 1 to 3 substituents selected from halogen, alkyl, haloalkyl, alkoxy, haloalkoxy, nitro, alkylthio, amino or di-substituted amino; di-substituted aminoxy; substituted iminoxy; di-substituted amino; substituted amido; or nitro;

X and Y taken together represent =O; or

X and R taken together may form the bridge,

wherein the carbonyl is attached to the phenyl ring, and Y is hydroxy, halogen, cyano, acyloxy, amino, substituted amino, alkoxycarbonyloxy, alkylsulfonyloxy, or carbamoyloxy which comprises reacting a compound of formula II

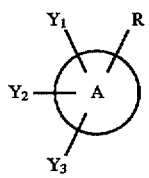

with a compound of formula III

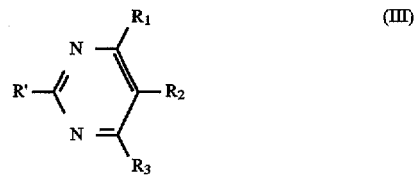

wherein R, $Y_1$, $Y_2$, $Y_3$, A, $R_1$, $R_2$ and $R_3$ have the meanings given above and R' represents cyano or a carboxylic ester group in the presence of a strong base.

In the definitions of formula I the various radicals are preferably within the following scopes:

A is preferably phenyl, but also pyridyl is preferred when linking to the —CXY— bridge through the 2-, 3- or 4-position.

The chain-type hydrocarbon radicals like alkyl, alkenyl, alkynyl, alkoxy, alkenyloxy, alkynyloxy, alkylthio, alkenylthio, alkynylthio, haloalkyl, haloalkoxy, acyloxy, alkoxycarbonyloxy, alkylsulfonyloxy, or the ester radicals of the carboxyl group or the thiocarboxyl group, or in the disubstituted carbamoyl group, or in the various amino, aminoxy, iminoxy, or amido groups in general are preferred if the number of carbon atoms is eight or lower.

Preferably $R_1$, $R_2$ and $R_3$ are each independently hydrogen, halogen, $C_{1-8}$alkyl, $C_{2-8}$alkenyl, $C_{2-8}$alkynyl, $C_{1-8}$alkoxy, $C_{2-8}$alkenyloxy, $C_{2-8}$alkynyloxy, $C_{1-8}$alkylthio, $C_{2-8}$alkenylthio or $C_{2-8}$alkynylthio, each of which may in turn be substituted by 1 to 6 halogen atoms; $C_{3-6}$cycloalkyl, a 5- or 6-membered heterocyclo$C_{1-8}$alkoxy, aryloxy, aryl$C_{1-8}$alkoxy or aryl$C_{1-8}$alkylthio each of which may be substituted by 1 to 3 substituents selected from halogen, $C_{1-8}$alkyl, $C_{1-8}$haloalkyl, $C_{1-8}$alkoxy, $C_{1-8}$haloalkoxy, nitro, $C_{1-8}$alkylthio, amino or di-$C_{1-8}$alkylamion, di-$C_{1-8}$alkylaminoxy; $C_{1-8}$alkyliminoxy; di-$C_{1-8}$alkylamino; $C_{1-8}$alkylamido; or nitro.

When X and R form the bridge —CO—O—, Y preferably is hydroxy, halogen, cyano, $C_{1-8}$acyloxy, amino, $C_{1-8}$alkylamino, di-$C_{1-8}$alkylamino, $C_{1-8}$alkoxycarbonyloxy, $C_{1-8}$alkylsulfonyloxy, or carbamoyloxy.

Salt forms of the carboxyl and thiocarboxyl groups include salts with inorganic or organic cations. Examples for inorganic cations are the alkaline or alkaline earth metal cations like lithium, sodium, potassium, magnesium or calcium, with sodium being preferred. Examples for organic cations are ammonium salts both from quaternary ammonium compounds and mono-, di- or trialkylamines. Especially preferred organic cations are dimethylammonium or isopropyl ammonium.

When, in the reaction according to the invention, a compound of formula II is employed wherein R represents a di-substituted carbamoyl group the compound of formula I thus obtained wherein X and Y taken together represent =O may, if desired, be converted to the corresponding compound of formula I wherein X and R taken together form the bridge

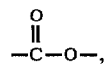

by ring closure in conventional manner.

When, in the reaction according to the invention, a compound of formula II is employed wherein R represents a carboxyl group in free form or in the form of a metal caboxylate the compound of formula I thus obtained wherein X and R taken together form the bridge

may, if desired, be converted into a compound of formula I wherein X and Y taken together represent =O by hydrolysis in a conventional manner.

As mentioned above, the reaction according to the invention is carried out in the presence of a strong base. Examples of such bases are lithium di-isopropylamide (LDA), n-butyllithium (n-BuLi), s-butyllithium (s-BuLi), n-hexyllithium.

The reaction is typically carried out in a solvent which is inert under the reaction conditions. Examples of such solvents include ethers such as diethylether, t-butylmethyl ether, tetrahydrofuran (THF) and dimethoxyethane; hydrocarbons such as pentane or hexane; aromatic hydrocarbons such as toluene; and cyclic hydrocarbons such as cyclohexane.

Particularly in the case of reactions where R is a carboxylic acid group, an amine such as tetramethylethylene diamine (TMEDA) can be added to the reaction mixture.

Reaction temperatures range from −70° to −20° during addition of the strong base and −70° to reflux temperature of the reaction mixture following addition of the compound formula III.

The reaction is preferably carried out under an inert gas such as nitrogen or argon.

Where a compound of formula II is employed wherein R is a carboxyl group in the form of its lithium salt it may be advantageous to carry out its preparation in a manner suitable for direct conversion into the di-lithium salt without isolation.

In cases where a compound of formula II is employed wherein R is a carboxyl group, this can be achieved preferably by reacting this compound with butyl lithium or lithium diisopropylamide. The reaction is preferably carried out in an inert solvent such as THF under inert gas atmosphere, e.g. argon at temperatures between −80° and 0° C.

In cases where a compound of formula II is employed wherein $Y_1$ represents halogen in ortho position to R this can also be achieved prefereably by reacting a compound of formula II wherein R is hydrogen with butyl lithium, or lithium diisopropylamide and carbon dioxide. The reaction is preferably carried out in an inert solvent such as THF under inert gas atmosphere e.g. argon at temperatures between −100° and −40° C., e.g. −70° C.

Ring closure of a compound of formula I wherein X and Y taken together represent =O to provide a compound of formula I wherein X and R taken together form the bridge

may be carried out in conventional manner e.g. by addition of an acid such as an inorganic acid e.g. hydrochloric acid (HCl), sulfuric acid ($H_2SO_4$) or an organic acid e.g. acetic acid (AcOH) or mixtures thereof.

Examples of suitable solvents for this reaction include water, acetic acid.

Reaction temperatures lie between room temperature and reflux temperature of the reaction mixture, especially −20° to +25°.

Hydrolysis of a compound of formula I wherein X and R taken together form the bridge

to provide a compound of formula I wherein X and Y taken together represent =O may be carried out in conventional manner e.g. by addition of a base e.g. sodium hydroxide or an amine base such as isopropylamine.

Examples of suitable solvents for this reaction include water optionally with an alcohol or a cyclic ether e.g. tetrahydrofuran or dichloromethane optionally with an alcohol or a cylic ether e.g. tetrahydrofuran (THF).

The compounds of formula I may be recovered in the preferred form with respect particularly to substituent R and converted between the various forms in conventional manner.

The compounds of formula I are useful i.a. as herbicides and are described along with other processes for their preparation, compositions containing them and their use as herbicides in U.S. Pat. No. 5,506,192 and EP-A-461,079 the contents of which are incorporated herein by reference.

Particularly preferred compounds of formula I are those wherein R is a carboxyl group which may be in the free acid or preferably salt form;

$Y_1$, $Y_2$ and $Y_3$ are attached to carbon atoms and are independently hydrogen or chlorine; and $R_1$ and $R_3$ are lower alkoxy and $R_2$ is hydrogen.

Particularly preferred are compounds wherein A is phenyl.

In the compounds of formula II, when employed in the process according to the invention, in addition to the preferences set out above for Y, R is preferably selected from a) di-substituted carbamoyl, especially dialkylcarbamoyl;
b) carboxyl.

In the compounds of formula III, when employed in the process according to the invention, in addition to the preferences set out above for $R_1$, $R_2$ and $R_3$, R' is preferably cyano or an ester moiety of formula

wherein R" represents $C_{1-10}$alkyl, $C_{2-10}$alkenyl or alkynyl or phenyl; R" is especially $C_{1-6}$alkyl, $C_{2-6}$alkenyl or phenyl.

Examples of carrying out the process according to the invention may be represented schematically as follows.

Scheme A

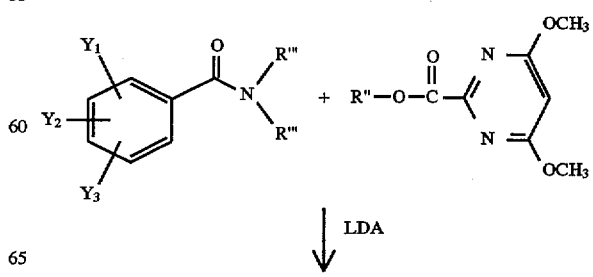

↓ LDA

-continued
Scheme A
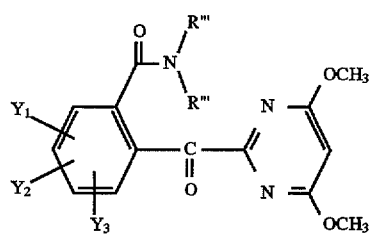
(optional) ↓ AcOH H₂O
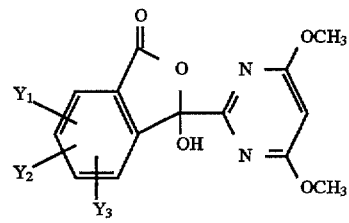
[R''' is a substituent e.g. as defined in U.S. Pat. No. 5,506,192, especially alkyl e.g. ethyl; R''''is as defined above e.g. i-butyl.]
Scheme B
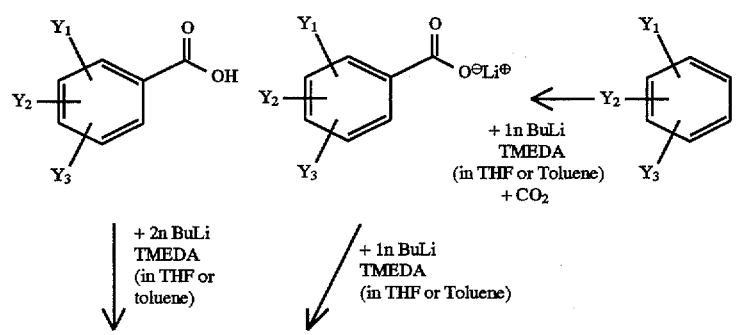
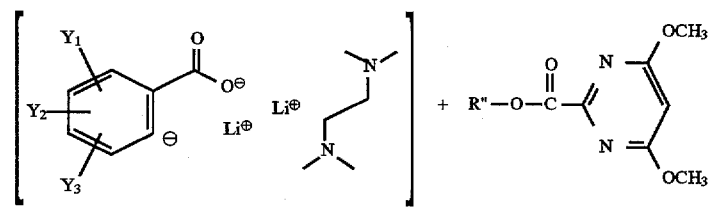
↓ H₂O
HCl
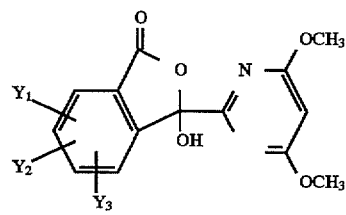
isopropylamine ($M^{\oplus} = iC_3H_7NH_3^{\oplus}$) | NaOMe ($M^{\oplus} = Na^{\oplus}$) ↓

-continued
Scheme B

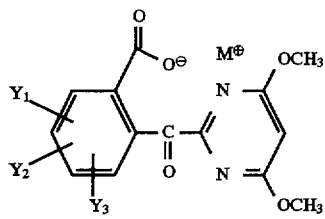

The following examples illustrate the invention, temperatures are in degrees centigrade.

EXAMPLE 1

Preparation of 4,7-dichloro-3-(4,6-dimethoxy-2-pyrimidinyl)-3-hydroxyphthalide 54.5 g of N,N-diethyl-2,5-dichlorobenzamide are dissolved in 265 ml of THF, cooled to −30° and 147.9 ml of 1.5M LDA added dropwise under $N_2$ atmosphere. Stirring is continued for 10 min. whereupon the reaction mixture is added via cannula under $N_2$ pressure to 44.4 g of 2-methylpropyl-2-(4,6-dimethoxypyrimidinyl)carboxylate dissolved in 175 ml of toluene at −30° with stirring. Following 5 min of additional stirring the reaction mixture is quenched with 250 ml of 1N HCl, 250 ml of toluene added and the organic phase washed with 2×250 ml of 1N HCl, water, brine and dried over $Na_2SO_4$. The solvent is distilled off under high vacuum at 70° and the residue dissolved in 200 ml AcOH, 1N HCl added until cloudy and further AcOH added until clear. Stirring is continued at RT for 3 days and the precipitate filtered, washed with a 1/1 mixture of AcOH/$H_2O$ and dried under vacuum at 70° to yield the title compound.

EXAMPLE 2

Preparation of 4,7-dichloro-3-(4,6-dimethoxy-2-pyrimidinyl)-3-hydroxyphthalide

A mixture of 1.91 g of 2,5-dichlorobenzoic acid, 19.1 ml of toluene, and 1.5 ml of N,N,N',N'-tetramethylethylenediamine is azeotroped for 3 hrs and cooled to −20°. 13.4 ml of 1.5M lithium diisopropylamide mono(tetrahydrofuran) in cyclohexane is then added by syringe over 10 min. After addition of 8.4 mL of the LDA solution a solution of 2.03 g of 2,2-dimethylpropyl-4,6-dimethoxy-2-pyrimidinecarboxylate in 4 mi of toluene is added dropwise over 7 minutes. The reaction mixture is stirred at −20°±5° for 1 hr with HPLC monitoring. The reaction mixture is quenched with water, 10 mL, stirred 10 min., and transferred to a separatory funnel. The mixture is allowed to stand 1 hr before separating the aqueous phase. The aqueous phase is acidified to pH 4.35 with dilute hydrochloric acid (conc. HCl, 5 mL, water, 5 mL). The precipitated solid is filtered, washed with water and dried by dissolving in dichloromethane, filtering through phase separation paper and concentration. This crude concentrate is digested with 4 ml of n-butyl acetate at 50° C. for 0.5 hr, cooled to room temperature and filtered. The product is washed with n-butyl acetate and hexane to give the title product, m.p. 197°–198°.

EXAMPLE 3

Preparation of 4,7-dichloro-3-(4,6-dimethoxy-2-pyrimidinyl)-3-hydroxyphthalide

A mixture of 1.22 g of TMEDA and 60 ml of THF is prepared under anhydrous condition and cooled to −10° with stirring. 36.03 g of a 20.5% solution of n-BuLi in cyclohexane is added and after 30 mins stirring the solution is cooled to −60°. A solution of 10.0 g of 2,5-dichlorobenzoic acid in 40 ml of THF is added over 10 min. at −60°. After a further 30 mins of stirring this solution is added over 15 min under argon pressure to a solution of 8.97 g of allyl 4,6-dimethoxypyrimidine-2-carboxylate in 60 ml of THF at −25° and the clear yellow solution cooled to −25°. After stirring at −20° for 60 mins, 60 ml of 10% HCl are added and the temperature allowed to rise to 13° with stirring over a 15 min period. The organic phase is separated and evaporated to yield a viscous residue to which is added 17 ml of methanol. The resulting suspension is cooled in an ice/water bath, filtered and the crystals washed with 2×10 ml methanol and dried under vacuum at 70° C. to yield the title product.

EXAMPLE 4

Preparation of 4,7-dichloro-3-(4,6-dimethoxy-2-pyrimidinyl)-3-hydroxyphthalide a) 4.0 g of N,N-diethyl-2,5-dichlorobenzamide are dissolved in 75 ml of toluene, cooled to −20° and 10.8 ml of 1.5M LDA added via syringe over 5 mins such that the temperature remains between −19° and −23°. This temperature is maintained for 5 mins and 2.0 g of 2-cyano-4,6-dimethoxy-pyrimidine in 25 ml toluene added dropwise at a temperature between −15° and −20°. After 10 mins the mixture is quenched with 25 ml 1N $H_2SO_4$, and the aqueous phase washed with ethylacetate. The combined organic phases are then washed with water and brine, dried and concentrated to give the intermediate product 2-[(4,6-dimethoxy-2-pyrimidinyl)-α-iminomethyl]-N,N-diethyl-2,5-dichlorobenzamide.

b) 3.1 g of 2-[(4,6-dimethoxy-2-pyrimidinyl)-α-iminomethyl]-N,N-diethyl-2,5-dichlorobenzamide dissolved in 50 ml of acetic acid and 50 ml of water and heated on an oil bath at 100° for 1 hour and refluxed for a further 2 hours and 2 ml of conc. HCl added. Refluxing is continued overnight and the mixture then cooled in an ice bath. The precipitate is filtered off, washed with water, air dried and concentrated. The residue is diluted with 100 ml of water, extracted with 3×50 ml of dichloromethane, washed with brine, dried and concentrated to give the title product.

EXAMPLE 5

Preparation of 4,7 dichloro-3-(4,6-dimethoxy-2-pyrimidinyl)-3-hydroxyphthalide 2.01 g of TMEDA and 79.3 ml of a 2.33M solution of butyl lithium in hexane are dissolved in 70 ml of THF at −10° under argon atmosphere. After 10 min the solution is cooled to −70° whereupon a solution of 22.64 g of 1,4-dichlorobenzene in 40 ml of THF is added within 1 hour. Stirring is continued for 20 min and then the solution is added via canula under argon pressure within 1 min into 14 g of $CO_2$ dissolved in 160 ml of THF at −70°. After completion of the addition another 7 g of $CO_2$ (dry ice) are added. Stirring is continued for 50 min. The excess $CO_2$ is removed in vacuo. To this mixture, 72.5 ml of a 2.33M solution of butyl lithium is added at −60° over 20 min and stirred for 1 hour.

The reaction mixture is added via canula under argon pressure within 15 min to 27.3 g of allyl 4,6-dimethoxypyrimidine-2-carboxylate in 180 ml THF at −30°. The mixture is stirred for 30 min at −25° and quenched with 180 ml of 10% hydrochloric acid. After stirring for 15 min the organic layer is separated and concentrated at 60° in vacuo. The residue is stirred with 50 ml of methanol for 30 min at 0°, filtered, washed with 50 ml of cold methanol and dried at 50° in vacuo to give the title product.

What is claimed:

1. A process for preparing a compound of formula I

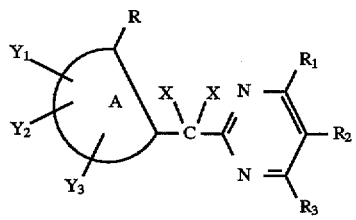

wherein

A is phenyl or pyridyl

R is a carboxyl group which may be in the form of the free acid or in ester or salt form, a thiocarboxyl group which may be in the form of the free acid or in ester form or a di-substituted carbamoyl group, $Y_1$, $Y_2$ and $Y_3$ are independently hydrogen or halogen;

$R_1$, $R_2$, and $R_3$ each is independently hydrogen; halogen; alkyl, alkenyl, alkynyl, alkoxy, alkenyloxy, alkynyloxy, alkylthio, alkenylthio or alkynylthio, each of which may in turn be substituted by 1 to 6 halogen atoms; cycloalkyl, heterocycloalkoxy, aryloxy, aralkoxy or aralkylthio each of which may be substituted by 1 to 3 substituents selected from halogen, alkyl, haloalkyl, alkoxy, haloalkoxy, nitro, alkylthio, or di-substituted amino; di-substituted aminoxy; substituted iminoxy; di-substituted amino; substituted amido or nitro;

$R_4$ is as defined for $Y_1$ except for hydrogen;

X and Y taken together represent =O; or

X and R taken together may form the bridge,

wherein the carbonyl is attached to the phenyl ring, and Y is hydroxy, halogen, cyano, acyloxy, amino, substituted amino, alkoxycarbonyloxy, alkylsulfonyloxy, or carbamoyloxy which comprises reacting a compound of formula II

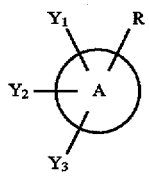

with a compound of formula III

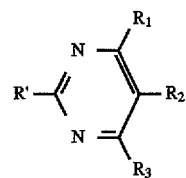

wherein R, Y, $Y_2$, $Y_3$, A, $R_1$, $R_3$ and $R_3'$ have the meanings given above and R' represents cyano or a carboxylic ester group in the presence of a strong base.

2. A process according to claim 1, wherein the strong base is selected from lithium diisopropylamine, n-butyllithium or s-butyllithium.

3. A process according to claim 1, wherein in the compound thus obtained R is a carboxy group in free acid or salt form.

4. A process according to claim 1, wherein in the compound thus obtained $Y_1$, $Y_2$ and $Y_3$ are attached to carbon atoms and are selected independently from hydrogen or chlorine.

5. A process according to claim 1, wherein in the compound thus obtained $R_1$ and $R_3$ are lower alkoxy and $R_2$ is hydrogen.

6. A process according to claim 1, wherein in the compound thus obtained A is phenyl.

7. A process according to claim 1, wherein the compound of formula II $Y_1$, $Y_2$ and $Y_3$ are attached to carbon atoms and are selected independently from hydrogen or chlorine and R is selected from dialkylcarbamoyl or carboxyl.

8. A process according to claim 1, wherein in the compound of formula III $R_1$ and $R_3$ are lower alkoxy, $R_2$ is hydrogen and R' is cyano or an ester moiety of formula

wherein R" is $C_{1-6}$alkyl, $C_{2-6}$alkenyl or phenyl.

9. A process according to claim 1, wherein in the compound obtained has the formula

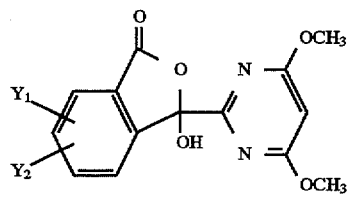

10. A process according to claim 1, wherein a compound of formula II is employed wherein R is a carboxyl group in the form of its lithium salt which is obtained from the corresponding compound wherein R is hydrogen, by reaction with butyl lithium and carbon dioxide.

11. A process according to claim 10 wherein the compound of formula II thus obtained is used directly in the next step without isolation.

* * * * *